United States Patent [19]

Tsujimura

[11] 4,291,985

[45] Sep. 29, 1981

[54] DUAL BEAM PHOTOMETER WITH ROTATING FILTER PLATE

[75] Inventor: Masatoshi Tsujimura, Fujimi, Japan

[73] Assignee: Nippon Denshoku Kogyo Co., Ltd., Tokyo, Japan

[21] Appl. No.: 118,307

[22] Filed: Feb. 4, 1980

[30] Foreign Application Priority Data

Apr. 17, 1979 [JP] Japan .................................. 54-47542

[51] Int. Cl.³ ........................ G01N 21/27; G01J 3/50
[52] U.S. Cl. .................................... 356/408; 356/418;
356/447
[58] Field of Search ............... 356/408, 418, 419, 236,
356/434, 447; 250/339

[56] References Cited

U.S. PATENT DOCUMENTS 4,029,419 6/1977 Schumann, Jr. et al. ............ 356/418

Primary Examiner—Vincent P. McGraw
Attorney, Agent, or Firm—Birch, Stewart, Kolasch & Birch

[57] ABSTRACT

A photometer comprising a light source, a rotating plate provided with a plurality of filter means having different wave lengths, a reference plate and a sample means, said rotating plate disposed between said light source and said reference plate and sample means, and a half-mirror and a reflection plate located between said light source and said rotating plate, said half-mirror and reflection plate being disposed so as to form a first light passage adapted to extend to the reference plate, and a second light passage adapted to extend to the sample means, whereby alternate radiation through one of said filter means against the reference plate and the sample means is made by the rotation of said rotary plate.

6 Claims, 5 Drawing Figures

DUAL BEAM PHOTOMETER WITH ROTATING FILTER PLATE

BACKGROUND AND SUMMARY OF THE INVENTION

The present invention relates to a light measuring device such as a chromatometer, a spectrometer, a colorimeter, a glossmeter, a white color meter, and the like.

In conventional types of light measuring devices of the kind mentioned above, a plurality of mechanisms are utilized to perform both spectrogram and alternative radiation procedures, and in view of this fact, the structure is very complicated and at the same time must accordingly have a large size and must be very expensive.

Furthermore, since the conventional types of devices use a plurality of mechanisms, there are introduced many trouble areas wherein the possibilities for generating errors against the measured values are increased, and thus it is difficult to obtain high reliable values.

In general, zero adjustment for use in making a measurement is manually performed when the adjustment is started, so that when the measuring time is continued for a long period, some variations of the light source and the light receiver are realized and thus it is difficult to obtain a correct measuring value differing from the zero adjustment initially obtained. At the same time, even if a zero adjustment can be made at a specified period of time, say midway through the metering operation, this operation is not performed due to the problems in making such a measurement.

It is therefore an object of the present invention to provide a photometer in which the disadvantages found in the conventional photometers are overcome and an extremely, highly reliable measuring value can be obtained.

It is another object of the present invention to provide a photometer in which both spectrogram and alternative radiation measurements may be performed by the rotation of one rotary plate provided with one mechanism, i.e. at least one filter element.

It is yet another object of the present invention to provide a photometer in which the zero adjustment may be automatically performed at every time a measurement is made with the variations of the light source and the light receiving element.

It is still a further object of the present invention to provide a photometer which possesses a simplified structure and its miniturization may be made to promote a rapid measuring operation.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from the detailed description.

According to the present invention, a half-mirror and a reflection plate are arranged in front of a light source to form one light passage extending to a reference plate and another light passage extending to a sample. A rotary plate provided with a plurality of filters having different wave lengths is installed in both light passages and an alternate radiation against the reference plate and the sample is caused by the rotation of the rotary plate.

The form of installation of the filters in the rotary plate of the present invention is made such that either one filter is alternatively positioned in one light passage extending to a reference plate or the other light passage extending to the sample, or a plurality of filters having different wave lengths which are installed in the rotary plate are initially positioned continuously in a light passage on the reference plate, and then continuously located in the light passage of the sample.

BRIEF DESCRIPTION OF THE DRAWINGS

The present invention will become more fully understood from the detailed description given hereinbelow and the accompanying drawings which are given by way of illustration only and, thus, are not limitative of the present invention, and wherein.

DESCRIPTION OF THE PREFERRED EMBODIMENTS

Figure 1:
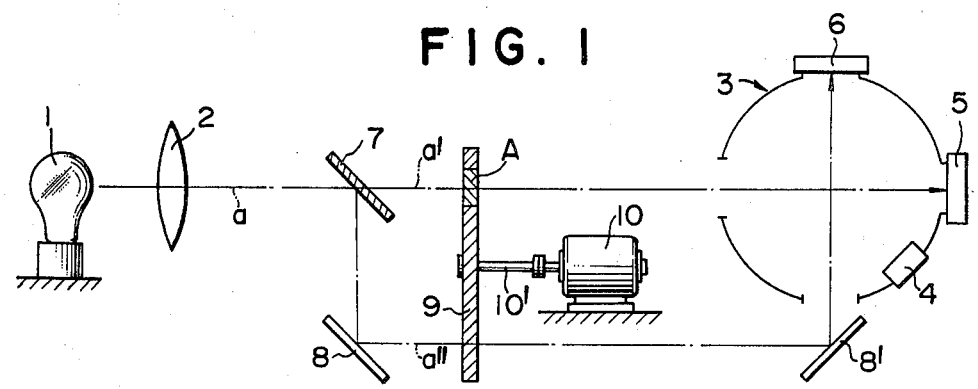
FIG. 1 is a schematic view of the system of the present invention.

FIG. 1 shows a schematic illustration of the photometer of the present invention in which element 1 is a light source, element 2 is a lense, element 3 is a multiplication ball, element 4 is a light receiving element installed at a proper location on the circumferential wall of the multiplication ball, element 5 is a reference plate, and element 6 is a sample. A half-mirror 7 for splitting the light into light passages a' and a" and reflection plates 8, 8', are installed in front of the light source 1 to form a light passage a' extending to the reference plate 5 and another light passage a" extending to the sample 6.

Figure 2:
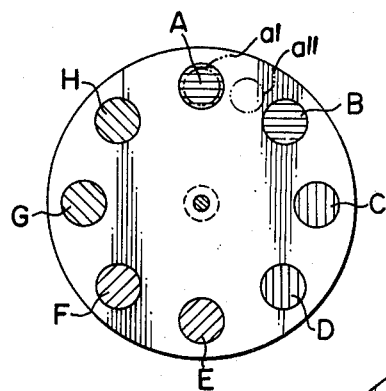
FIGS. 2 and 3 are front elevational views of the rotary plate showing the filter and the relationship of the position between the light passages a', a" and the filter.
Figure 3:
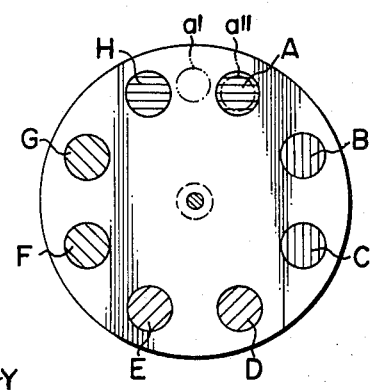

In the light passage a' extending to the reference plate 5 and in the light passage a" extending to the sample 6 is installed a rotary plate 9 for performing the spectrogram and alternative radiation procedures. The rotary plate 9 is rotated as illustrated in FIGS. 2 and 3 with the rotating shaft 10' of the motor 10 being inserted into the center of the rotary plate 9 and fixed thereto. Around the circumference of the rotary plate 9 are arranged a plurality of filters A, B, C, D, E, F, G, and H having different wavelengths. Installation spacing between each of the filters is such that an alternative radiation against the reference plate 5 and sample 6 can be performed. Thus, when the filter A is located in the light passage a' for radiation against the reference plate 5, the solid portion of the rotary plate 9, which is located in the light passage a', interrupts the light passage a" from radiating against the sample 6. Then by rotating the rotary plate 9, the filter A is located in light passage a" for radiation against the sample 6, and the rotary plate, in turn, interrupts the light passage a' to the reference plate 5. Thus the reference plate 5 and the sample 6 are alternately radiated and the reflected light is received by the light receiver 4.

The arrangement of the filter A to H or the alternative radiating arrangement is not restricted to the procedure wherein the above-mentioned reference plate 5 and the sample 6 are alternately radiated. Thus, the reference plate 5 can be radiated a plurality of times using filters having different wavelengths. Thereafter, it is also possible to provide a plurality of radiations against sample 6 using said filters. This form of the filter plate is shown in FIG. 4.

Figure 4:
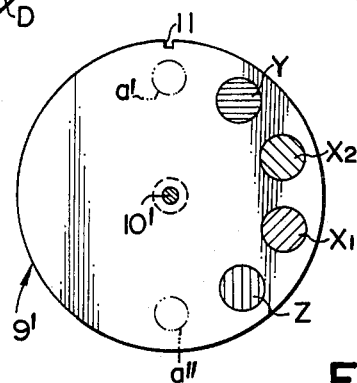
FIG. 4 is a front elevational view of the rotary plate having a different installational form of the filters.

A rotary plate 9' shown in FIG. 4 is arranged such that four kinds of filters (Y), (X$_2$), (X$_1$), and (Z) are arranged on one side of the plate with equal spacing being provided therebetween. On the rotary plate 9' is placed a position indicator 11 for obtaining a zero adjustment by the simultaneous shielding of both light passages a', a'' for radiating against the reference plate 5 and for radiating against the sample 6. Zero adjustment is performed at every rotation of the rotary plate 9' and thus the variation of the light source 1 and the light receiving means 4 may always be accommodated.

Figure 5:
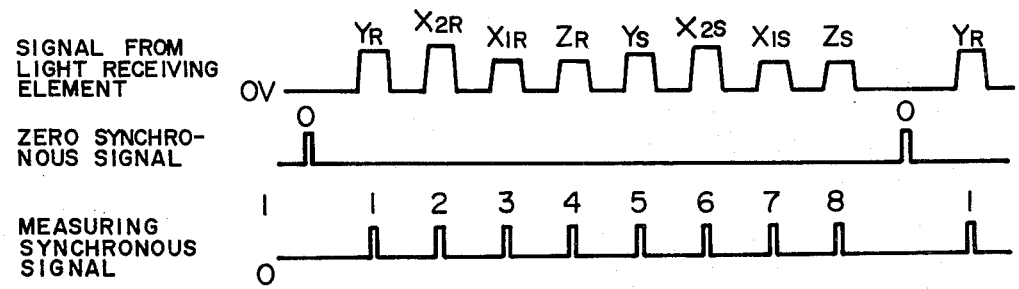
FIG. 5 is a measuring time chart when the rotary plate of FIG. 4 is used to perform a measurement.

FIG. 5 is a measuring time chart for when the rotary plate 9' of FIG. 4 is rotated to provide a measurement. A value of the signal is used to sense the output value when a synchronizing signal is fed thereto.

The synchronizing signals 1 to 4 are those made by the reference plate 5 and the synchronizing signals 5 to 8 are made by the sample 6. The value is continuously stored in the memory.

The metering value Y is calculated as follows:

$$Y = \frac{Y_s - T_o}{Y_R - T_o} \times W$$

where,
R = value at the reference plate;
s = value at the sample;
w = value of the white reference plate; and
$T_o$ = value when both light passages are shielded The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:
1. A photometer comprising
a light source,
a rotating plate provided with a plurality of filter means having different wave lengths,
a reference plate and a sample means, said rotating plate disposed between said light source and said reference plate and sample means, and
a half-mirror and a reflection plate located between said light source and said rotating plate, said half-mirror and reflection plate being disposed so as to form a first light passage adapted to extend to the reference plate, and a second light passage adapted to extend to the sample means, whereby alternate radiation through one of said filter means against the reference plate and the sample means is made by the rotation of said rotary plate.

2. The photometer of claim 1 wherein motor means is operatively connected with said rotating plate for rotating said plate.

3. The photometer of claim 1 wherein a light receiving element is operatively associated with said reference plate and said sample means for receiving light therefrom.

4. The photometer of claim 1 wherein the reflection plate, the sample means and the light receiving element are combined in a multiplication ball.

5. The photometer of claim 4 wherein an additional reflection plate is disposed near the multiplication ball for directing the second light passage to the sample means.

6. The photometer of claim 1 wherein the filter means are so disposed that both the first and second light passages can be simultaneously shielded from the reference plate and the sample means by the rotation of said rotating plate thereby performing a zero adjustment at every rotation of the rotating plate.

* * * * *